(12) United States Patent
Bracken et al.

(10) Patent No.: US 8,834,425 B2
(45) Date of Patent: Sep. 16, 2014

(54) SECUREMENT SYSTEM EMPLOYING POLYMERIC GEL

(75) Inventors: Ronald L. Bracken, Monroe, GA (US); Vasu Nishtala, Snellville, GA (US); Larry White, Duluth, GA (US); Robert Young, Loganville, GA (US)

(73) Assignee: C.R. Bard, Inc., Covington, GA (US)

( * ) Notice: Subject to any disclaimer, the term of this patent is extended or adjusted under 35 U.S.C. 154(b) by 0 days.

(21) Appl. No.: 12/174,537

(22) Filed: Jul. 16, 2008

(65) Prior Publication Data

US 2009/0137962 A1    May 28, 2009

Related U.S. Application Data

(60) Provisional application No. 60/949,937, filed on Jul. 16, 2007.

(51) Int. Cl.
*A61M 5/32* (2006.01)
*A61M 5/14* (2006.01)
*A61L 24/04* (2006.01)
*A61L 24/00* (2006.01)

(52) U.S. Cl.
CPC ............ *A61M 5/1418* (2013.01); *A61L 24/046* (2013.01); *A61L 24/0031* (2013.01); *A61L 24/0089* (2013.01)
USPC .......................................... 604/179; 604/174

(58) Field of Classification Search
CPC ..................... A61M 25/02; A61M 2025/0253; A61M 2025/0266; A61M 2025/0273
USPC .................................. 604/174–180
See application file for complete search history.

(56) References Cited

U.S. PATENT DOCUMENTS

| | | | |
|---|---|---|---|
| 3,046,984 | A | 7/1962 | Eby |
| 3,167,072 | A | 1/1965 | Stone et al. |
| 3,194,235 | A | 7/1965 | Cooke |
| 3,288,137 | A | 11/1966 | Lund |
| 3,630,195 | A | 12/1971 | Santomieri |
| 3,700,574 | A | 10/1972 | Kehr |
| 3,826,254 | A | 7/1974 | Mellor |

(Continued)

FOREIGN PATENT DOCUMENTS

| | | |
|---|---|---|
| CA | 1 311 977 | 12/1992 |
| CA | 1 318 824 | 6/1993 |

(Continued)

OTHER PUBLICATIONS

U.S. Appl. No. 09/136,271, applicant Steven F. Bierman, filed Aug. 18, 1989.

(Continued)

*Primary Examiner* — Kami A Bosworth
(74) *Attorney, Agent, or Firm* — Knobbe Martens Olson & Bear LLP

(57) ABSTRACT

A gel pad for use with a retainer for securing a medical article. The gel pad is formed from a soft, tacky elastomer. A first surface of the gel pad is placed in contact with a patient's skin. A second surface that faces in an opposite direction away from the first surface receives the retainer. The retainer has a channel configured to retain at least a portion of the medical article. In some embodiments, a securement member is employed to affix the retainer relative to the patient. A securement system including the gel pad and retainer is further disclosed along with a method of securing a medical article to a patient.

25 Claims, 7 Drawing Sheets

(56) References Cited

U.S. PATENT DOCUMENTS

| | | | |
|---|---|---|---|
| 3,900,026 | A | 8/1975 | Wagner |
| 3,901,226 | A | 8/1975 | Scardenzan |
| 4,082,094 | A | 4/1978 | Dailey |
| 4,129,128 | A | 12/1978 | McFarlane |
| D252,822 | S | 9/1979 | McFarlane |
| 4,193,174 | A | 3/1980 | Stephens |
| 4,224,937 | A | 9/1980 | Gordon |
| 4,250,880 | A | 2/1981 | Gordon |
| 4,333,468 | A | 6/1982 | Geist |
| 4,470,410 | A | 9/1984 | Elliott |
| 4,484,913 | A | 11/1984 | Swauger |
| 4,516,968 | A | 5/1985 | Marshall et al. |
| 4,517,971 | A | 5/1985 | Sorbonne |
| 4,563,177 | A | 1/1986 | Kamen |
| 4,632,670 | A | 12/1986 | Muller |
| 4,633,863 | A | 1/1987 | Filips et al. |
| 4,645,492 | A | 2/1987 | Weeks |
| 4,669,458 | A | 6/1987 | Abraham et al. |
| 4,711,636 | A | 12/1987 | Bierman |
| 4,737,143 | A | 4/1988 | Russell |
| 4,846,807 | A | 7/1989 | Safadago |
| 4,852,844 | A | 8/1989 | Villaveces |
| 4,863,432 | A | 9/1989 | Kvalo |
| 4,898,587 | A | 2/1990 | Mera |
| 4,976,698 | A | 12/1990 | Stokley |
| 4,997,421 | A | 3/1991 | Palsrok et al. |
| 5,037,397 | A | 8/1991 | Kalt et al. |
| 5,074,847 | A | 12/1991 | Greenwell et al. |
| 5,084,026 | A | 1/1992 | Shapiro |
| 5,112,313 | A | 5/1992 | Sallee |
| 5,116,324 | A | 5/1992 | Brierley et al. |
| 5,137,519 | A | 8/1992 | Littrell et al. |
| 5,192,273 | A | 3/1993 | Bierman |
| 5,192,274 | A | 3/1993 | Bierman |
| 5,215,532 | A | 6/1993 | Atkinson |
| 5,238,010 | A | 8/1993 | Grabenkort |
| 5,290,248 | A | 3/1994 | Bierman et al. |
| D347,060 | S | 5/1994 | Bierman |
| 5,314,411 | A | 5/1994 | Bierman et al. |
| 5,328,487 | A | 7/1994 | Starchevich |
| 5,354,282 | A | 10/1994 | Bierman |
| 5,356,391 | A | 10/1994 | Stewart |
| 5,370,627 | A | 12/1994 | Conway |
| 5,395,344 | A | 3/1995 | Beisang et al. |
| 5,413,120 | A | 5/1995 | Grant |
| 5,413,562 | A | 5/1995 | Swauger |
| D359,120 | S | 6/1995 | Sallee et al. |
| 5,456,671 | A | 10/1995 | Bierman |
| D364,922 | S | 12/1995 | Bierman |
| 5,539,020 | A * | 7/1996 | Bracken et al. ................ 523/212 |
| 5,551,421 | A * | 9/1996 | Noureldin et al. ....... 128/207.17 |
| D375,355 | S | 11/1996 | Bierman |
| D375,356 | S | 11/1996 | Bierman |
| 5,577,516 | A | 11/1996 | Schaeffer |
| 5,578,013 | A | 11/1996 | Bierman |
| D377,831 | S | 2/1997 | Bierman |
| 5,605,546 | A | 2/1997 | Wolzinger et al. |
| 5,664,581 | A | 9/1997 | Ashley |
| 5,681,290 | A | 10/1997 | Alexander |
| 5,685,859 | A | 11/1997 | Kornerup |
| 5,686,096 | A | 11/1997 | Khan et al. |
| 5,690,616 | A | 11/1997 | Mogg |
| 5,693,032 | A | 12/1997 | Bierman |
| 5,702,371 | A | 12/1997 | Bierman |
| 5,722,959 | A | 3/1998 | Bierman |
| 5,728,053 | A | 3/1998 | Calvert |
| 5,800,402 | A | 9/1998 | Bierman |
| 5,800,410 | A | 9/1998 | Gawreluk |
| 5,810,781 | A | 9/1998 | Bierman |
| D399,954 | S | 10/1998 | Bierman |
| 5,827,230 | A | 10/1998 | Bierman |
| 5,827,239 | A | 10/1998 | Dillon et al. |
| 5,833,666 | A | 11/1998 | Davis et al. |
| 5,833,667 | A | 11/1998 | Bierman |
| 5,855,591 | A | 1/1999 | Bierman |
| 5,885,254 | A | 3/1999 | Matyas |
| 5,897,519 | A | 4/1999 | Shesol et al. |
| 5,944,696 | A * | 8/1999 | Bayless et al. ................ 604/174 |
| 6,050,934 | A | 4/2000 | Mikhail et al. |
| D425,619 | S | 5/2000 | Bierman |
| 6,099,509 | A | 8/2000 | Brown et al. |
| 6,113,577 | A | 9/2000 | Hakky et al. |
| 6,132,398 | A | 10/2000 | Bierman |
| 6,132,399 | A | 10/2000 | Shultz |
| 6,213,979 | B1 | 4/2001 | Bierman |
| 6,224,571 | B1 | 5/2001 | Bierman |
| 6,231,547 | B1 | 5/2001 | O'Hara |
| 6,231,548 | B1 | 5/2001 | Bassett |
| 6,258,066 | B1 | 7/2001 | Urich |
| 6,283,945 | B1 | 9/2001 | Bierman |
| 6,290,676 | B1 | 9/2001 | Bierman |
| 6,361,523 | B1 | 3/2002 | Bierman |
| 6,375,639 | B1 | 4/2002 | Duplessie |
| 6,413,240 | B1 | 7/2002 | Bierman et al. |
| 6,428,516 | B1 | 8/2002 | Bierman et al. |
| 6,436,073 | B1 | 8/2002 | Teichert |
| 6,447,485 | B2 | 9/2002 | Bierman |
| 6,447,486 | B1 | 9/2002 | Tollini |
| 6,471,676 | B1 | 10/2002 | DeLegge et al. |
| 6,482,183 | B1 | 11/2002 | Pausch |
| 6,491,664 | B2 | 12/2002 | Bierman |
| 6,500,154 | B1 | 12/2002 | Hakky et al. |
| D469,530 | S | 1/2003 | Gomez |
| D470,936 | S | 2/2003 | Bierman |
| 6,517,522 | B1 | 2/2003 | Bell |
| 6,551,285 | B1 | 4/2003 | Bierman |
| 6,572,588 | B1 | 6/2003 | Bierman et al. |
| 6,582,403 | B1 | 6/2003 | Bierman et al. |
| 6,616,635 | B1 | 9/2003 | Bell |
| 6,626,890 | B2 | 9/2003 | Nguyen et al. |
| 6,652,487 | B1 | 11/2003 | Cook |
| 6,663,600 | B2 | 12/2003 | Bierman et al. |
| 6,689,104 | B2 | 2/2004 | Bierman |
| D492,411 | S | 6/2004 | Bierman |
| 6,770,055 | B2 | 8/2004 | Bierman et al. |
| 6,786,892 | B2 | 9/2004 | Bierman |
| 6,809,230 | B2 | 10/2004 | Hancock et al. |
| 6,827,705 | B2 | 12/2004 | Bierman |
| 6,827,706 | B2 | 12/2004 | Tollini |
| 6,827,707 | B2 | 12/2004 | Wright et al. |
| 6,834,652 | B2 | 12/2004 | Altman |
| 6,837,875 | B1 | 1/2005 | Bierman |
| 6,866,652 | B2 | 3/2005 | Bierman |
| D503,977 | S | 4/2005 | Bierman |
| 6,951,550 | B2 | 10/2005 | Bierman |
| 6,972,003 | B2 | 12/2005 | Bierman |
| 6,979,320 | B2 | 12/2005 | Bierman |
| 6,981,969 | B2 | 1/2006 | Chavez et al. |
| 7,014,627 | B2 | 3/2006 | Bierman |
| 7,018,362 | B2 | 3/2006 | Bierman |
| 7,070,580 | B2 | 7/2006 | Nielsen |
| 7,090,660 | B2 | 8/2006 | Roberts et al. |
| D528,206 | S | 9/2006 | Bierman |
| 7,153,291 | B2 | 12/2006 | Bierman |
| 7,354,421 | B2 | 4/2008 | Bierman |
| 7,377,472 | B2 | 5/2008 | Brown et al. |
| 8,251,956 | B2 | 8/2012 | Bierman et al. |
| 2002/0068904 | A1 | 6/2002 | Bierman et al. |
| 2002/0099360 | A1 | 7/2002 | Bierman |
| 2002/0133121 | A1 | 9/2002 | Bierman |
| 2003/0055382 | A1 | 3/2003 | Schaeffer |
| 2003/0229313 | A1 | 12/2003 | Bierman |
| 2004/0102736 | A1 | 5/2004 | Bierman |
| 2004/0111067 | A1 | 6/2004 | Kirchhofer |
| 2004/0138624 | A1 | 7/2004 | Bierman |
| 2004/0204685 | A1 | 10/2004 | Wright et al. |
| 2005/0182367 | A1 | 8/2005 | Walborn |
| 2005/0215953 | A1 | 9/2005 | Rossen |
| 2005/0288635 | A1 | 12/2005 | Davis et al. |
| 2006/0015076 | A1 | 1/2006 | Heinzerling et al. |
| 2006/0064063 | A1 | 3/2006 | Bierman |
| 2006/0135944 | A1 | 6/2006 | Bierman |
| 2006/0184127 | A1 | 8/2006 | Bierman |
| 2006/0184129 | A1 | 8/2006 | Bierman |

(56) References Cited

U.S. PATENT DOCUMENTS

| | | |
|---|---|---|
| 2006/0217669 A1 | 9/2006 | Botha |
| 2006/0247577 A1 | 11/2006 | Wright |
| 2006/0264836 A1 | 11/2006 | Bierman |
| 2006/0270995 A1 | 11/2006 | Bierman |
| 2009/0143740 A1 | 6/2009 | Bierman et al. |
| 2010/0298778 A1 | 11/2010 | Bracken |

FOREIGN PATENT DOCUMENTS

| | | |
|---|---|---|
| EP | 0356683 | 3/2000 |
| WO | WO 94/21319 | 9/1994 |
| WO | WO 97/15337 | 5/1997 |
| WO | WO 99/55409 | 11/1999 |

OTHER PUBLICATIONS

Design U.S. Appl. No. 29/179,916, applicant Steven F. Bierman, filed Apr. 14, 2003.

International Search Report for App. No. PCT/US03/25622, mailed Mar. 10, 2004.

* cited by examiner

SECUREMENT SYSTEM EMPLOYING POLYMERIC GEL

CROSS-REFERENCE TO RELATED APPLICATION

This application claims the benefit of U.S. provisional application No. 60/949,937, entitled "MEDICAL LINE SECUREMENT SYSTEM EMPLOYING HIGH FRICTION POLYMERIC GEL," filed on Jul. 16, 2007, which is hereby incorporated by reference in its entirety.

BACKGROUND OF THE INVENTION

1. Field of the Invention

This invention relates to a gel pad and securement system employing the gel pad for securing a medical article to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line can be secured to the patient in a variety of ways. Most commonly, this involves taping the catheter or medical line to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical article can additionally lead to the build up of adhesive residue on the outer surface of the catheter or medical line. This residue can result in contaminants adhering to the catheter itself, increasing the likelihood of infection of the insertion site. This residue can also make the catheter or medical article stickier and more difficult to handle for healthcare providers. Further, moisture may build up where the patient's skin is covered by the tape. As such, there remains a need for an improved medical article securement system for use with a patient that overcomes the problems associated with current designs.

SUMMARY OF THE INVENTION

The systems and methods disclosed herein have several features, no single one of which is solely responsible for its desirable attributes. Without limiting the scope as expressed by the claims that follow, its more prominent features will now be discussed briefly.

In one aspect, provided is a securement system for use with a medical article. The securement system includes a retainer having a body member, the body member having a longitudinal channel formed through the body member and a central axis, the channel being configured to retain at least a portion of the medical article within the body member, a gel pad formed from a soft, tacky elastomer, the gel pad having a first surface and a second surface, the first surface for placing upon the skin of a patient and the second surface for supporting the retainer thereupon and a securement strap, the securement strap for securing the retainer and gel pad to the patient.

In another aspect provided is a method of securing a medical article to a patient. The method includes the steps of: supplying a gel pad formed from a soft, tacky elastomer, the gel pad having a first surface and a second surface, the first surface for placing upon the skin of a patient and the second surface for placing the retainer thereupon, affixing a medical article to a retainer having a body member, the body member having a longitudinal channel formed through the body member and a central axis, the channel being configured to retain at least a portion of the medical article within the body member and securing the retainer and gel pad to the patient with a securement strap, the securement strap.

In one form, the gel pad is formed by curing an organopolysiloxane composition.

In another form, the organopolysiloxane composition includes a vinyl-containing high viscosity organopolysiloxane or a blend of high viscosity vinyl-containing organopolysiloxanes, a low viscosity organopolysiloxane or a blend of low viscosity organopolysiloxanes, a reinforcing filler, a platinum catalyst and a hydrogen containing polysiloxane copolymer In yet another form, the retainer further includes a pair of mounting wings, each mounting wing extending longitudinally and positioned below and spaced apart from the longitudinal channel and wherein the securement strap includes a pair of securement strap members, each securement strap member affixed to one of the pair of mounting wings of the retainer.

In still yet another form, the securement strap members are formed from a Velcro® material. These and other features will be apparent from the detailed description taken with reference to accompanying drawings.

In another aspect, provided is a securement system for use with a medical article, including a gel pad for placing upon the skin of a patient; and a retainer supported at least in part by the gel pad.

In yet another aspect, provided is a method of securing a medical article to a patient. The method includes providing a gel pad; affixing a medical article to a retainer having a body member, the body member having a longitudinal channel formed through the body member, the channel being configured to retain at least a portion of the medical article within the body member; and locating the retainer relative to the patient so that at least a portion of the gel pad is disposed between at least a portion of the retainer and the patient.

In still another aspect, provided is a cured organopolysiloxane composition for use with a securement device that secures a medical article to a patient. The composition includes a vinyl-containing high viscosity organopolysiloxane; a low viscosity organopolysiloxane; a reinforcing filler; a platinum catalyst; and a hydrogen containing polysiloxane copolymer.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

DETAILED DESCRIPTION OF PREFERRED EMBODIMENTS

Figure 1:
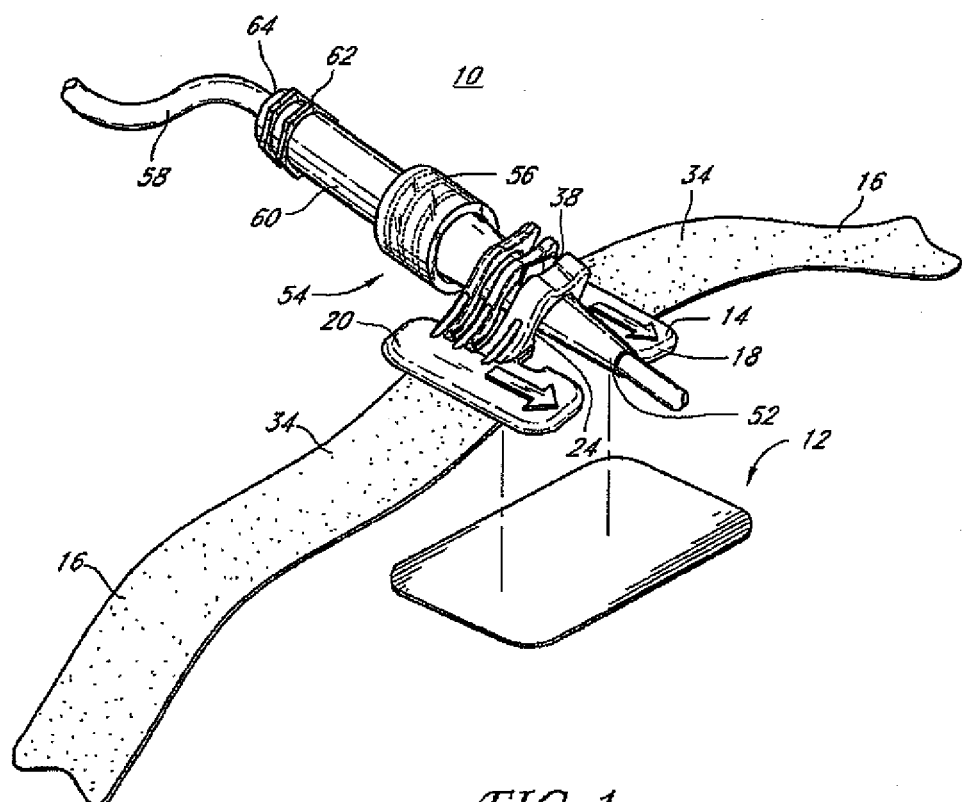
FIG. 1 is an exploded, perspective view showing a securement system according to a preferred embodiment of the present invention with a medical article affixed to a retainer for subsequent placement upon a gel pad.

The following description and examples illustrate preferred embodiments of the present securement system in detail which is disclosed in the context of use with an exemplary medical device. The principles of the present invention, however, are not limited to medical devices. It will be understood by those of skill in the art in view of the present disclosure that the securement system described can be used with medical articles, including, but not limited to: catheters, fluid delivery tubes, electrical wires, and other medical devices or their components. One skilled in the art may also find additional applications for the devices and systems disclosed herein. Thus, the illustrations and descriptions of the securement system in connection with the medical devices are merely exemplary of some possible applications of the securement system.

To assist in the description of these components of the securement system, the following coordinate terms are used. Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise. A "longitudinal axis" is generally parallel to a portion of the catheter hub, the connector fitting or other medical article retained by the securement system, as well as parallel to the axis of a channel of the retainer, through which the medical article extends. A "lateral axis" is normal to the longitudinal axis. A "transverse axis" extends normal to both the longitudinal and lateral axes. The "longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein.

Also, the terms "proximal" and "distal", which are used to describe the present securement system, are used consistently with the description of the exemplary applications. Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. In the form illustrated herein, the arrows on the securement device point in the direction toward the insertion site (i.e., in the proximal direction).

The term "alkyl" refers to radicals having from 1 to 8 carbon atoms per alkyl group, such as methyl, ethyl, propyl, butyl, pentyl, hexyl, octyl and the like. The term "alkenyl" refers to radicals having from 2 to 8 carbon atoms such as, vinyl, allyl and 1-propenyl. The term "aryl" refers to mononuclear and binuclear aryl radicals such as, phenyl, tolyl, xylyl, naphthyl and the like; mononuclear aryl alkyl radicals having from zero (i.e. no alkyl group or a bond) to 8 carbon atoms per alkyl group such as benzyl, phenyl and the like. The term "monovalent hydrocarbon radicals" includes hydrocarbon radicals such as alkyl, alkenyl and aryl.

The term "tacky" means that the tacky, gal pad has an adhesive property that is somewhat sticky to the touch, enabling the pad or sheet padding to be readily attached to a limb or other area of a patient's body, yet is easily removed, i.e. is releasably attached. The term "macerating" means to soften the skin over a period of time, especially as a result of the skin being wetted or occluded. The term "limb" refers to the paired appendages of the body used especially for movement or grasping, including the legs, knees, shins, ankles, feet, toes, arms, elbows, forearms, wrists, hands, fingers or any part thereof. The term "curing" refers to any process by which the raw or uncured polysiloxanes containing reinforcing agents are convened to a finished product, i.e. the soft, tacky, reinforced polysiloxane elastomer.

Various aspects will now be described with reference to specific forms or embodiments selected for purposes of illustration. It will be appreciated that the spirit and scope of the securement system disclosed herein is not limited to the selected forms. Moreover, it is to be noted that the figures provided herein are not drawn to any particular proportion or scale, and that many variations can be made to the illustrated embodiments. Brief introductions to some of the features, which are common to the described embodiments of the securement systems, are now described. In the illustrated forms, the arrows on the securement device point in the direction toward the insertion site (i.e., in the proximal direction).

The forms disclosed herein provide a securement system for securing a medical article to a patient. The medical article may have an elongated body. The elongated body cooperates with a retainer to arrest movement of the medical article in longitudinal, lateral, and/or transverse directions when placed within the retainer.

In each of the forms described below, the retainer has a body member that includes a channel formed there through.

The medical article is installed or removed from the channel. A gel pad is disposed between at least a portion of the retainer and the patient's skin. The gel pad has little or no ability to induce maceration of the skin, due in part to its permeability for transporting water vapor from the skin through the gel pad. Such an arrangement induces little or no maceration when applied to the skin for an extended period.

The retainer may also include at least one abutment that cooperates with at least one contact point or surface on the medical article. The one or more abutments of the retainer extend generally normal to the axis of the channel and can be, for example, but without limitation, a surface, a wall of a slot, a ridge, a protuberance, or like structures. The abutment cooperates with the one or more contact points or surfaces of the medical article to inhibit longitudinal movement of the medical article through the channel. For example, the abutment could be a surface on the distal end of the retainer that acts against at least a portion of a radially extending member of the medical article. In this way, the medical article will be limited in it proximal movement (i.e., movement toward the patient) once the radially extending member contacts or abuts against the distal end of the retainer.

The retainer may also include in one form at least one support that may be disposed on the underside of the retainer at a position lower than the access opening. The support may include left and right mounting wings that are integral with the body member for contact with the gel pad, as will be described in detail herein below.

As disclosed herein, other constructions also inhibit contact between the skin and the retainer, as well as between the skin and the retained portion of the medical article.

Reference is now made to FIGS. 1-12, wherein like numerals are used to designate like parts throughout. FIG. 1 is an exploded perspective view of a securement system 10 configured in accordance with a preferred embodiment of the present invention. As shown in FIG. 1 the illustrated securement system 10 includes two main components: a gel pad 12 and a retainer 14. The gel pad 12 is placed on a patient's skin with the retainer 14 being placed on the exposed surface of the gel pad 12.

In some embodiments, the gel pad 12 adheres to the patient's skin 12 and/or the retainer 14 adheres to the gel pad 12. Adhesive layers may be employed in the contact regions between the patient, gel pad 12 and/or retainer 14. The gel pad 12 material may provide a degree of self adhesion to the patient and/or retainer 14 without adding adhesive layer(s).

The securement system may further include a securement member 16 for securing the retainer 14 to the patient. Depending on the strengths of adhesion, if any, between the gel pad 12 and the patient and between the retainer 14 and the gel pad 12, the securement system may not need the securement member 16. Regardless of whether additional securement is desired, for embodiments that include a securement member 16, one or both contact regions between the gel pad 12 and the patient and between the retainer 14 and the gel pad 12 need not form an adhesion bond. In such embodiments, the securement member 16 secures the retainer 14 to the patient. For example, the securement member 16 may be affixed to the retainer 14 and indirectly compress the gel pad 12 against the patient's skin by compressing the retainer 14 towards the patient.

The securement member 16 can be, for example, a strap, clip, or adhesive member that secures the retainer 14 to the patient. For example, a strap can extend from the retainer 14 and wrap around a limb or other portion of the patient to thereby secure the retainer 14. Alternatively, the strap employs an adhesive layer for securing the strap to the patient. In such an embodiment, the strap need not extend around the limb of the patient but instead contacts a sufficiently large region of the patient's skin beyond the outer periphery of the retainer 14 to thereby adhere to the patient.

The strap can extend from one or both sides of the retainer 14. For embodiments that have a strap extending from only one side of the retainer 14, the free end of the strap may, for example, secure to another portion of the strap via a hook and loop type fastener or other similar structure, a surface of the retainer 14, a latch member on the retainer 14, or through a loop on the retainer 14. The latch can be similar to a conventional belt buckle with the free end of the strap securing thereto. For embodiments that have a strap extending from both sides of the retainer 14, the straps may secure to each other via a hook and loop type fastener or other similar structure.

For embodiments that have a clip, the clip can extend from one or both sides of the retainer 14 to surround at least a portion of the patient's limb. Preferably, the clip surrounds at least 180 degrees of the patient's torso or limb. Unlike a flexible strap, the clip can be formed so as to have a memory or shape which generally matches the portion of the patient around which the clip is to be secured. Such an arrangement allows the clip to secure the retainer 14 to the patient without having to secure the ends of the clip. For such embodiments, the gel pad 12 or additional gel pads 12 may, or may not, be placed between the securement member 16 and the patient in the regions beyond the outer periphery of the retainer 14.

For embodiments that have an adhesive, the adhesive can be disposed between the retainer 14 and the gel pad 12 and/or between the retainer 14 and the patient's skin so as to secure the retainer 14 relative to the patient. For embodiments that have an adhesive disposed between the retainer 14 and the gel pad 12, the adhesive need only be disposed on a portion of the contacting surfaces between the retainer 14 and the gel pad 12. The adhesive may be in the form of a layer on some or all of one or both of the retainer 14 and gel pad 12. The gel pad 12 material may provide a degree of self adhesion to the patient and/or retainer 14 without adding adhesive layer(s).

The retainer 14 may include portions that extend beyond the contact surface formed between the retainer 14 and the gel pad 12. For example, an outer periphery of the retainer 14 can extend beyond the outer periphery of the gel pad 12. The outer periphery of the retainer 14 can include an adhesive on some or all of its downwardly facing surface for adhering to the patient's skin. In this way, the retainer 14 can be directly secured to the patient. Of course, one or more types of securement members 16 may be employed in a single securement system.

As is illustrated in the embodiment of FIG. 1, the securement member 16 is in the form of a strap extending from both sides of the retainer 14. The illustrated retainer 14 includes a left footing mounting wing 18 and a right footing mounting wing 20. Each mounting wing is disposed upon the gel pad 12, when the securement system 10 is affixed to a patient. The mounting wings 18 and 20 extend in a lateral direction away from a center of the retainer 14, as shown.

As noted above, the securement system 10 can form a component of a catheterization system that also includes one or more medical articles, such as connector fittings, catheters, hubs, catheter adaptors, fluid supply lines, or other articles suitable for securement via securement system 10. Referring also to FIGS. 2-7, an opening in the retainer 14 is aligned with a medical article. The medical article is inserted between the mounting wings 18 and 20, through the opening, and into the retainer 14. The gel pad 12 is then placed upon the skin of the patient. The retainer 14 and secured medical article are placed on the gel pad 12 and secured to the patient. As explained above, the retainer 14 may be secured to the patient with or without the use of a securement member. As is illustrated, securement member in the form of a strap 16, which may, for example, be produced from a material such as Velcro®, is then deployed so as to at least restrict, if not prevent, lateral and transverse movement of the retained section of the medical article. Additional features of the securement system 10 can restrict if not prevent, longitudinal and rotational movement of the retained section of the medical article. The illustrated form may be used with a catheter adapter or hub, as will be described more fully herein below.

Gel Pad

Figure 8:
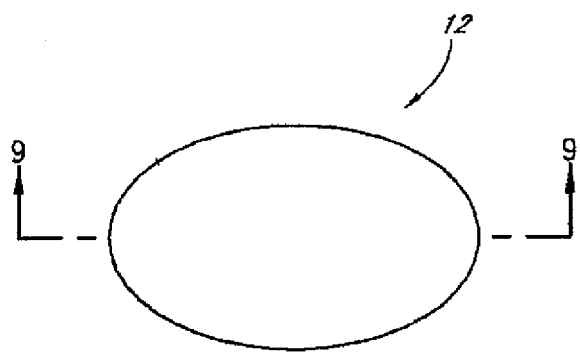
FIG. 8 is a top plan view of the gel pad from FIG. 1.
Figure 9:
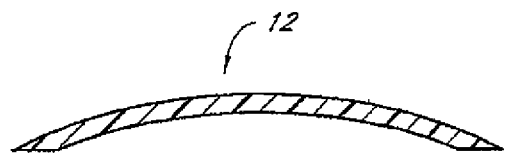
FIG. 9 is a cross-section view through the gel pad taken along line 9-9 of FIG. 8.
Figure 10:
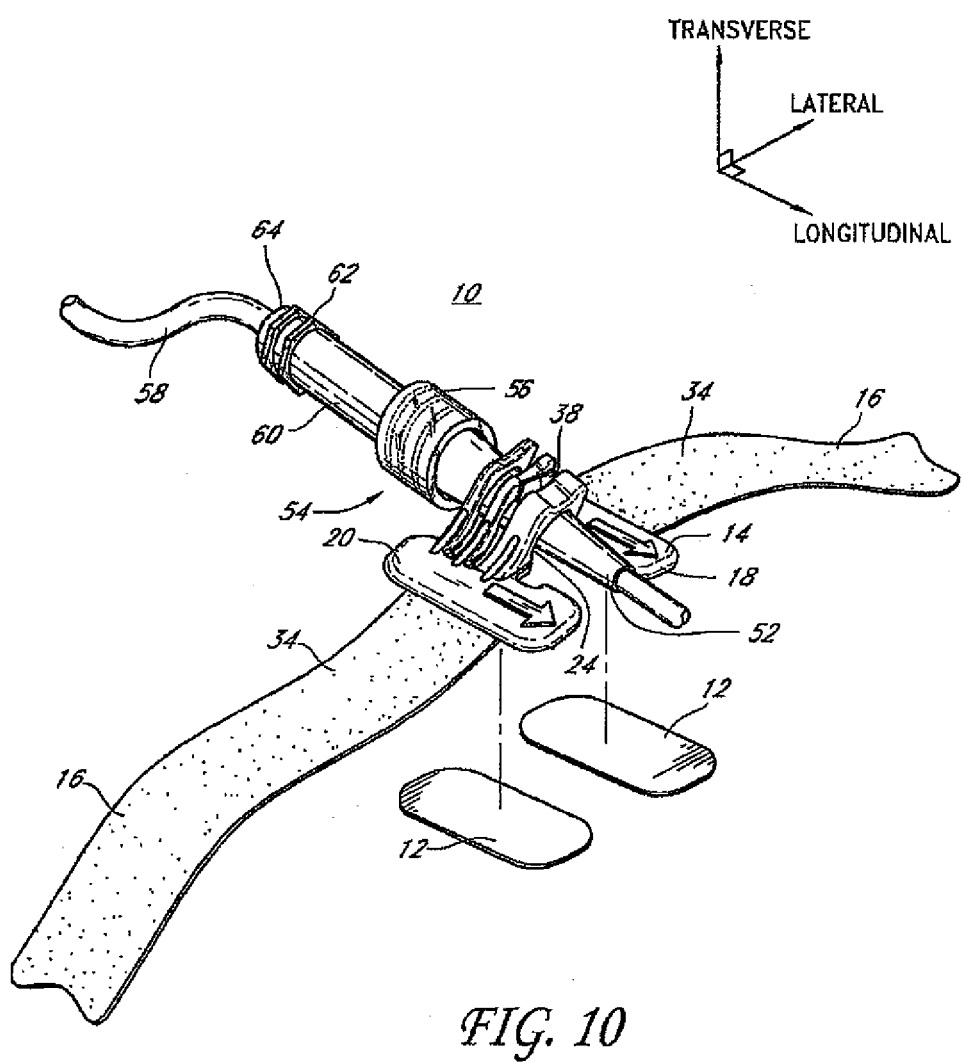
FIG. 10 is an exploded, perspective view showing a securement system according to another preferred embodiment of the present invention with a medical article affixed to a retainer for subsequent placement upon a plurality of gel pads.

FIGS. 1 and 8-12 illustrate various forms of the gel pad 12, with FIGS. 8-9 showing the gel pad 12 apart from the rest of the securement system 10. The general shape of the illustrated gel pad 12 is generally oval, although other shapes are effective depending upon the particular application. As may be appreciated, such other shapes contemplated include, for example, but not by way of limitation, circular, trapezoidal, rectangular, square, etc. In some embodiments, the shape of the gel pad 12 parallels that of a retainer component. For example, the shape of the gel pad 12 may be similar to that of mounting wings 20, as shown in FIG. 10.

The gel pad 12 may be about the same size, smaller or bigger than a retainer component. For example, the gel pad may be about at least 10%, 25%, 50%, 75%, 100%, 125%, 150%, or 200% the size of a retainer component. The gel pad may be about less than about 10%, 25%, 50%, 75%, 100%, 125%, 150%, or 200% the size of a retainer component. When a larger gel pad 12 is used, it may be easier to position a retainer 14 on the gel pad 12. However, smaller gel pads 12 may be less expensive to manufacture.

In some embodiments, a plurality of gel pads 12 is used, as shown in FIG. 10. Each of the gel pads may, for example, be placed under a different component or side of the retainer 14. For example, each of two mounting wings 20 may be positioned on a separate gel pad 12. In such instances, the gel pads 12 may be able to be applied first to the retainer 12 before being applied to a patient's skin. It will be understood that when the term "gel pad" is used herein in a singular form, it is also considered that a plurality of gel pads may be used.

Figure 11:
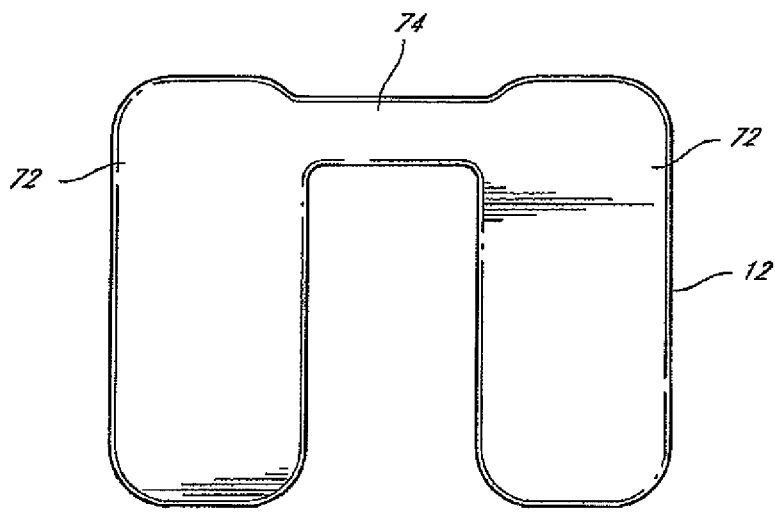
FIG. 11 is a top plan view of another embodiment of a gel pad with two segments and one connecting portion.
Figure 12:
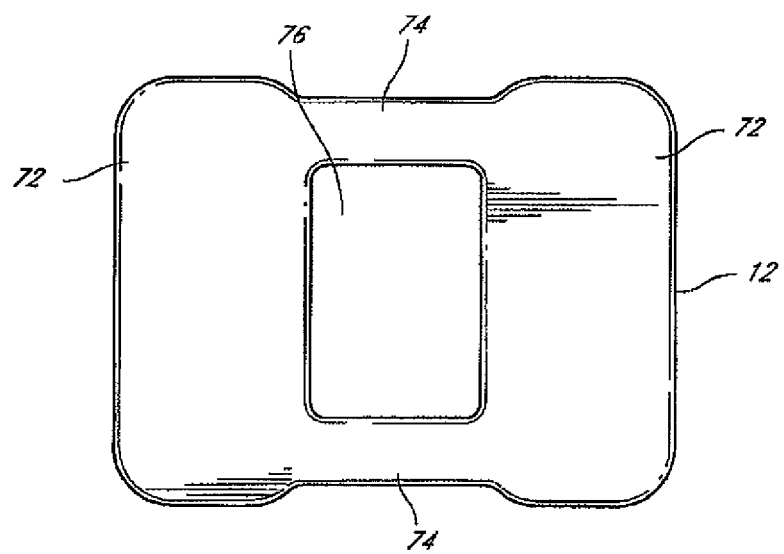
FIG. 12 is a top plan view of another embodiment of a gel pad with two segments and two connecting portions.

In some embodiments, a single gel pad 12 comprises a plurality of segments 72, as shown in FIGS. 11 and 12. Each one of the segments 72 may have a size and/or shape similar to that of a retainer component, such as a mounting wing 20. The segments may be connected by one or more connecting portions 74. The connecting portion may be made of the same material as the segments 72 or of a different material. In some embodiments, the flexibility and/or adhesiveness of the connecting portion 74 is different from that of the segments 72. The gel pad 12 may comprise a gel pad opening 76. The gel pad opening 76 may parallel that of the retainer's lower opening 26, such that when the retainer 12 is positioned on the gel pad, the gel pad opening 76 aligns with the lower opening 26. In some embodiments, the connecting portion/s 74 are configured such that there is no gel pad opening 76, as shown in FIG. 11. In some embodiments, a portion of the gel pad 12 has a shape paralleling a portion of a securement strap 16.

Referring now to FIGS. 8 and 9, gel pad 12 may be produced from a high coefficient of friction, tacky, gel-like material. In one form, gel pad 12 may be a cured, tacky, reinforced polysiloxane elastomer. Gel pad 12 may be formed by curing a mixture of a lower alkenyl-functional polysiloxane, such as a vinyl containing polysiloxane, and a hydrogen containing polysiloxane copolymer containing active hydrogen groups. In this regard, the term "hydrogen" refers to active hydrogen that is directly bonded to a silicon atom (Si—H), for example, silicon hydrides and hydrogen containing organopolysiloxanes. Such amounts of the hydrogen containing polysiloxane copolymer will be dependent upon factors such as the molar ratio of alkenyl radicals to active hydrogen in the uncured composition and the nature of these components, including such variables as polymer chain length, molecular weight and polymer structure.

The organopolysiloxane elastomers disclosed herein, prior to curing, have a ratio of hydrogen to alkenyl radicals of less than 1.5, or 0.5 to 1.2, which imparts tack or tackiness to the end product produced therefrom. The tackiness is believed to be caused by the partially crosslinked organopolysiloxane elastomers.

It should be recognized that the tacky gel pad 12 possesses the requisite tack property throughout the entire gel pad 12. However, surface tack can be modified to be greater than or less than the interior tack. Quantitative measurements of tackiness can be made using a suitable tack tester, such as a Polyken® probe tack tester, a rolling ball tack tester, a peel tester or combinations thereof. Tack can be tested with the Polyken® probe tester in accordance with any suitable procedure, such as American Society For Testing and Materials (ASTM) Designation: D2979-71 (Reapproved 1982), Standard Test Method for Pressure-Sensitive Tack of Adhesives Using an Inverted Probe Machine, pp. 187-189, from the Annual Book of ASTM Standards, Vol. 15.09. The Polyken® probe tack tester is the trademark of the Kendall Company, under license by Testing Machines Inc., Mineola, Long Island, N.Y. Tack can also be tested with a rolling ball tack tester in accordance with Pressure Sensitive Tape Council, Test Methods for Pressure Sensitive Tapes, 9th Edition, PSTC-6, revised August, 1989, pp. 29-30 or ASTM D3121. Tack can also be tested with a peel tester in accordance with Pressure Sensitive Tape Council, Test Methods for Pressure Sensitive Tapes, 9th Edition, PSTC-1, revised August 1989, pp. 21-22. The tacky, cushioning layer can be artificially aged prior to tack testing using conventional accelerating aging procedures, such as by exposing the layer to ultraviolet light, elevated temperatures and/or elevated humidity.

The tacky gel pad 12 disclosed herein has little or no ability to induce maceration of the skin, due in part, to its permeability for transporting water vapor from the skin through the gel pad. Thus, the tacky layer disclosed herein can provide a third, tri-function of inducing little or no maceration when applied to the skin for an extended period. One test method for evaluating water vapor transmission is ASTM Designation: E96-80, Standard Test Methods for Water Vapor Transmission of Materials, edited May 1987, pp. 629-633.

Determinations of the hardness of the gel pad 12 can be made with any suitable durometer for testing hardness. One test method entails resting the edge of a Shore 00 durometer on a material, applying a presser foot to the material without shock and taking the average of three readings. Further details for testing hardness can be found in ASTM Test Method D2240. One of ordinary skill in the art will appreciate that elastomers measured by the Shore 00 durometer scale are softer than those measured by the Shore A durometer scale.

Representative vinyl-containing high viscosity organopolysiloxanes of formula (1) suitable for preparing a base material include, but are not limited to the following.

$$R^4-\underset{\underset{R}{|}}{\overset{\overset{R^1}{|}}{Si}}-\underset{\underset{R_x}{|}}{\overset{\overset{R}{|}}{OSi}}-\underset{\underset{R_y}{|}}{\overset{\overset{R^2}{|}}{OSi}}-\underset{\underset{R}{|}}{\overset{\overset{R^1}{|}}{OSi}}-R^5 \quad (1)$$

| Polymer | R | R² | R³ | R⁴ | R⁵ | x | y |
|---|---|---|---|---|---|---|---|
| 1 | —CH₃ | —CH₃ | —C₆H₅ | —CH₃ | —C₂H₃ | 925 | 50 |
| 2 | —CH₃ | —CH₃ | —C₆H₅ | —C₂H₃ | —C₂H₃ | 809 | 45 |
| 3 | —CH₃ | —CH₃ | —C₆H₅ | —C₂H₃ | —C₂H₃ | 611 | 41 |
| 4 | —CH₃ | —CH₃ | —C₆H₅ | —C₂H₃ | —C₂H₅ | 471 | 30 |
| 5 | —CH₃ | —CH₃ | —CH₃ | —C₂H₃ | —CH₃ | 600 | 20 |
| 6 | —CH₃ | —CH₃ | —CH₃ | —C₂H₃ | —C₂H₅ | 600 | 20 |

Representative low viscosity organopolysiloxanes of formula (2) suitable for use in preparing a base material include, but are not limited to the following.

$$R^1-\underset{\underset{R}{|}}{\overset{\overset{R^3}{|}}{Si}}-\underset{\underset{R_w}{|}}{\overset{\overset{R}{|}}{OSi}}-\underset{\underset{R_z}{|}}{\overset{\overset{R^2}{|}}{OSi}}-\underset{\underset{R}{|}}{\overset{\overset{R^3}{|}}{OSi}}-R^6 \quad (2)$$

| Polymer | R | R² | R³ | R⁴ | R⁶ | x | z |
|---|---|---|---|---|---|---|---|
| 1 | —CH₃ | —C₂H₃ | —C₆H₅ | —CH₃ | —CH₃ | 138 | 13 |
| 2 | —CH₃ | —C₂H₃ | —C₆H₅ | —CH₃ | —CH₃ | 192 | 39 |
| 3 | —CH₃ | —C₂H₃ | —CH₃ | —CH₃ | —CH₃ | 125 | 25 |
| 4 | —CH₃ | —CH₃ | —CH₃ | —CH₃ | —CH₃ | 90 | 20 |
| 5 | —CH₃ | —CH₃ | —CH₃ | —CH₃ | —CH₃ | 125 | 25 |

The base material prepared from the vinyl-containing high viscosity organopolysiloxanes of formula (1) and the low viscosity organopolysiloxanes of formula (2) can be admixed with a copolymer containing dimethyl and methyl hydrogen siloxanes. The amount of hydrogen-containing organopolysiloxane used should be sufficient to achieve a ratio of alkenyl radicals to hydrogen in the uncured composition of less than 1.2.

The elastomers are reinforced with a suitable reinforcing agent or filler such as titanium dioxide, calcium carbonate, lithopone, zinc oxide, zirconium silicate, silica aerogel, iron oxide, diatomaceous earth, silazane-treated silica, precipitated silica, fumed silica, mined silica, glass fibers, magnesium oxide, chromic oxide, zirconium oxide, aluminum oxide, alpha quartz, calcined clay and the like, as well as various reinforcing silica fillers taught in U.S. Pat. No. 3,635,743, the contents of which are hereby incorporated by reference in its entirety, or mixtures of any of the above, or a filler selected from silazane treated silica, precipitated silica and fumed silica or mixtures thereof. In one form, the reinforcing filler is a highly reinforcing silica filler with a surface area ranging from about 80 to about 400 square meters/gram (m²/g), or from about 200 to about 400 m²/g. Typically the reinforcing agent is mixed with the vinyl-containing high viscosity organopolysiloxane (1) and low viscosity organopolysiloxane (2) prior to addition of the hydrogen containing polysiloxane copolymer. The reinforcing filler can be employed in the uncured composition in an amount ranging from 10 to about 70 parts per 100 parts of the uncured composition, or from 15 to about 40 parts, or from about 20 to about 30 parts. In the cured tacky, reinforced cushioning layer, such amounts correspond to about ten to about 70% by weight, or from about 15 to about 40%, or from about 20 to about 30%.

The durometer or hardness of the polysiloxane elastomers disclosed herein can be lowered (i.e. made softer) by incorporating low viscosity polysiloxanes into the uncured composition. Representative low viscosity polysiloxanes include polydimethylsiloxane fluids or vinyl-containing polydimethylsiloxane fluids. The molecular weight average of the plasticizer can range from about 750 to about 30,000. The low viscosity polysiloxanes can be employed in an amount ranging from about zero to about 50% by weight of the uncured composition, or from about 10 to about 30%.

The polysiloxane elastomers disclosed herein possess suitable hardness, tensile strength, elongation and tear strength, as based upon standard elastic materials testing. Unreinforced polysiloxane compositions must be enclosed in an envelope or other supporting means, i.e. foam impregnation, in order to maintain the shape or durability of an article produced therefrom. In contrast, the high coefficient of friction, tacky, polysiloxane gel pad 12 disclosed herein is viscoelastic and has a measurable hardness, tensile strength, elongation and/or tear strength.

Further, the tacky, reinforced polysiloxanes disclosed herein can retain their elastic properties after prolonged action of compressive stresses, a property known as compression set. Compression set is an indicator of durability. According to ASTM Designation: D395-85, Standard Test Methods for Rubber Property Compression Set, pp. 34-35, the actual stressing service may involve the maintenance of a definite deflection, the constant application of a known force, or the rapidly repeated deformation and recovery resulting from intermittent compressive forces. Though the latter dynamic stressing, like the others, produces compression set, its effects as a whole are simulated more closely by compression flexing or hysteresis tests. Therefore, compression set tests are considered to be mainly applicable to service conditions involving static stresses.

Tests are frequently conducted at elevated temperatures. In a first method utilizing static stresses, a test specimen is compressed to a deflection and maintained under this condition for a specified time and at a specified temperature. In a second method utilizing static stresses, a specified force is maintained under this condition for a specified time and at a specified temperature. After application of the specified deflection or specified force the residual deformation of a test specimen is measured 30 minutes after removal from a suitable compression device in which the specimen has been subjected for a definite time to compressive deformation under specified conditions. After measurement of the residual deformation, the compression set as specified in the appropriate method is calculated according to ASTM D395-85 equations.

When produced in accordance herewith, gel pads 12 may be prepared to exhibit the following physical properties: a durometer hardness of from about 5 to 55 units (Shore 00), a tensile strength of from about 20 to about 800 psi, a minimum elongation of from about 250 to about 1100 percent, a tear strength of from about 5 to about 200 lb/in, a polyken probe tack of about 10 to about 450 grams, a rolling ball tack of about 0 to about 3 inches and a peel test value of from about 0.02 to about 80 lb/in. Of course the gel pad 12 is not limited to the above described properties.

The gel pad 12 can be prepared using techniques such as molding, liquid injection molding, transfer molding, casting and the like. Gel pad 12 can be preformed into a desired shape for use with securement system 10, supplied in a sheet form, which may be cut to the desired shape prior to use or the gel material provided in a kit form. A catalyst may be provided in a first container and the other components premixed and provided in a second container. In the latter case, a mold is provided and the components mixed, poured into the mold and cured. Curing can be with or without heat.

Such curing can be achieved by increasing the molecular weight of the uncured polysiloxane elastomers to the extent desired through crosslinking, using heating or standing at ambient, as described U.S. Pat. No. 3,445,420, the contents of which are hereby incorporated by reference in its entirety. Generally, the degree to which the uncured polysiloxane composition can be partially crosslinked can range from about 30 to about 90%, based upon the alkenyl-containing polysiloxane, or from about 30 to about 60%.

In use, gel pad 12 is preferably arranged with respect to the retainer 14 such that the tip of the medical article does not extend beyond the front edge of the mounting wings 18 and 20 when the medical article is properly inserted within the retainer 14.

Retainer

Figure 2:
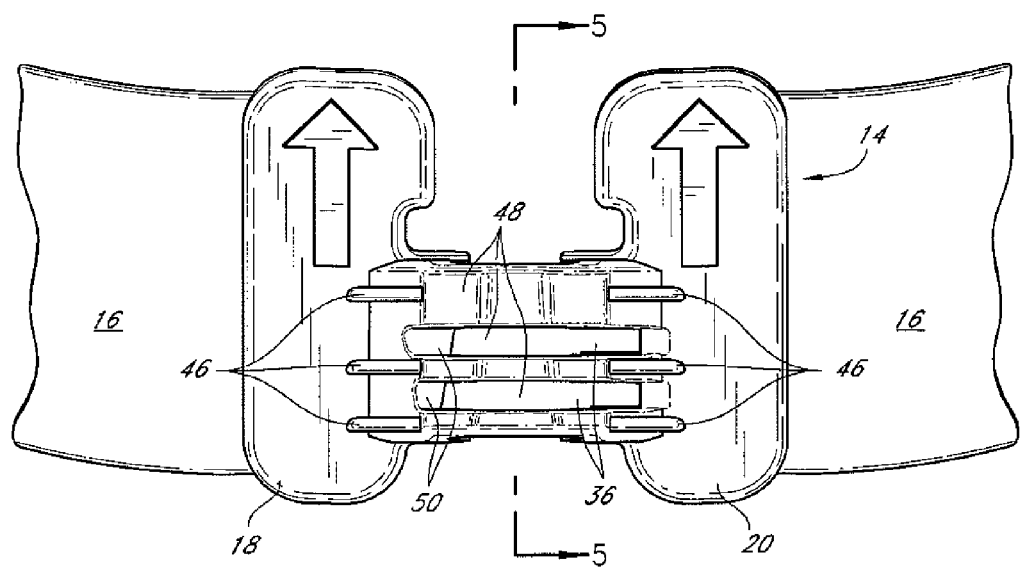
FIG. 2 is a top plan view of the retainer and portions of the securement members from FIG. 1.
Figure 3:
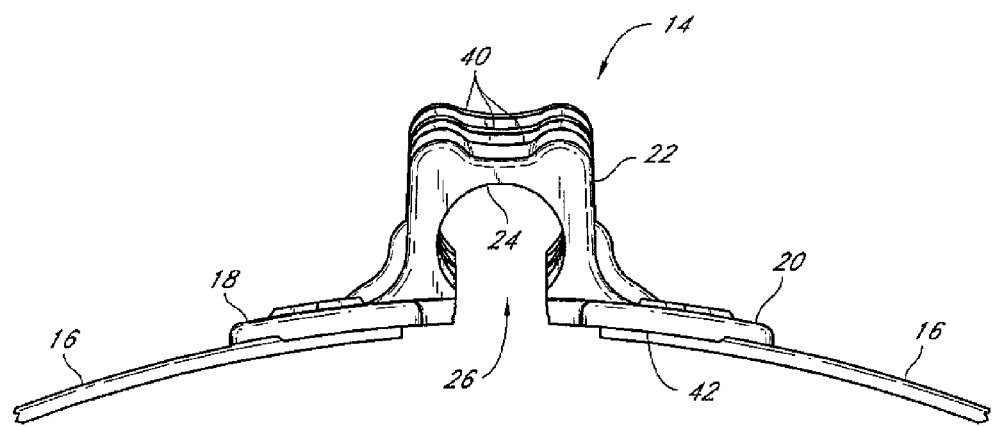
FIG. 3 is a front side view of the retainer and portions of the securement members from FIG. 2.
Figure 4:
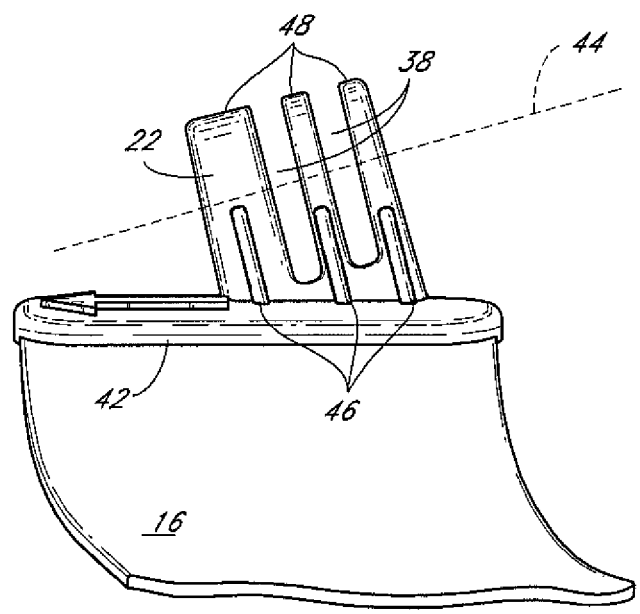
FIG. 4 is a side view of the retainer and a portion of one of the securement members from FIG. 2.
Figure 5:
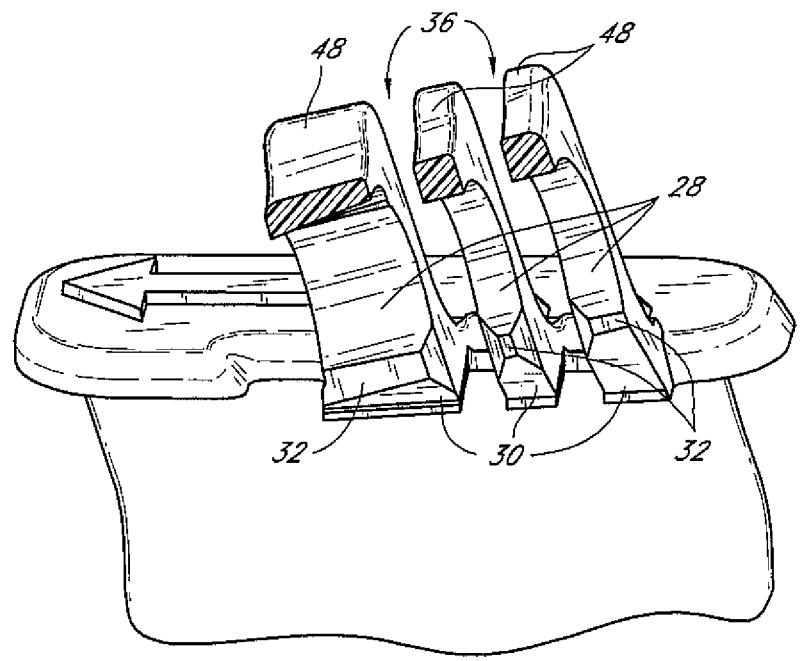
FIG. 5 is a cross-section view of the retainer taken along line 5-5 of FIG. 2.

One form of retainer 14 is described with reference to FIGS. 1-7 and 10. FIG. 2 is a top plan view of the retainer 14 which limits rotation of an installed catheter hub as well as arrests movement of the catheter hub in the longitudinal, lateral and transverse directions. FIG. 3 is a front side view of the retainer 14 from FIG. 2 and illustrates a body member 22 and footings/side mounting wings 18 and 20 that extend in a lateral direction from either side of the body member. As shown in FIGS. 4 and 5, the body member 22 is elongated in the longitudinal direction and comprises a generally parallelepiped shape. The longitudinal dimension of the body member 22 may be sufficiently long to provide stability to the retained portion of the medical article along its length. In this way, the longitudinal length of the retained portion is sufficient to inhibit the rocking of the medical article within the retainer 14. Also, the lateral dimension of the body member 22 of the retainer desirably allows the healthcare provider to easily and naturally grip the body member.

With reference to FIG. 3, the inner side of the body member 22 faces towards the patient's skin when in use and defines an inverted central channel 24. The inverted channel 24 extends on the underside of the body member 22 in a longitudinal direction for receiving a section of the catheter hub in the illustrated form.

The channel 24 is capable of receiving a portion or length of the medical article and is generally configured to house, or grip, and to secure this portion of the medical article. In the form illustrated herein in FIGS. 2 through 7, the central channel 24 has a generally semi-circular cross-sectional shape. An inner surface contour of the central channel 24 is selected depending on the geometry of the portion of the medical article to be retained. For example, in a retainer 14 that is configured to retain a portion of a medical article that has a constant outer diameter, the central channel 24 has a constant radius along its length. In contrast, in a retainer 14 configured to retain a portion of a medical article that has a tapering outer surface, the central channel 24 may have a tapering inner surface and a radius that varies along the channel length.

Additional embodiments of the central channel 24 of the retainer can comprise a plurality of different radii and/or tapering regions. For example, as disclosed in U.S. Pat. No. 7,014,627, the contents of which are hereby incorporated by reference in their entirety, the channel 24 can have two sections: a first proximal section having a generally uniform cross-sectional size along its length while a second distal section has a tapering shape along its length. An abutment wall may be provided to form a transition between these two sections of the channel. These sections of the channel 24 can also both be tapered or straight (i.e., have a generally uniform radius along the length of the section) or the distal section can be straight and the proximal section can be tapered. In this way, the size and shape of the central channel 24 can be chosen to match or to approximate the size and shape of the medical article or portion thereof, e.g., the catheter hub, to be retained.

By matching the inner surface contour of the central channel 24 to the outer surface of the secured portion of a medical article, a more effective securement may be achieved. In addition or in the alternative, effective securement can also be achieved by the engagement of one or more abutment surface of the retainer 14 with one or more contact surfaces on the medical article. Each abutment surface can cooperate with a contact surface on the medical article to inhibit movement of the medical article relative to the retainer. Exemplary abutment surfaces and contact surfaces are described below with reference to FIG. 1.

Although the central channel 24 can be formed in various shapes depending upon the desired application (e.g., depending upon a shape of the retained portion of the medical article for which the retainer is designed to be used), the central channel 24 desirably has a sufficient length in the longitudinal direction to stabilize the connector fitting, catheter hub, or other medical article, rather than act as a fulcrum for the fitting, as mentioned above. That is, the retainer 14 receives a sufficient length of the medical article to inhibit movement of the medical article in the lateral, longitudinal and transverse direction (i.e., to inhibit yaw, pitch and axial movement of the article).

Figure 6:
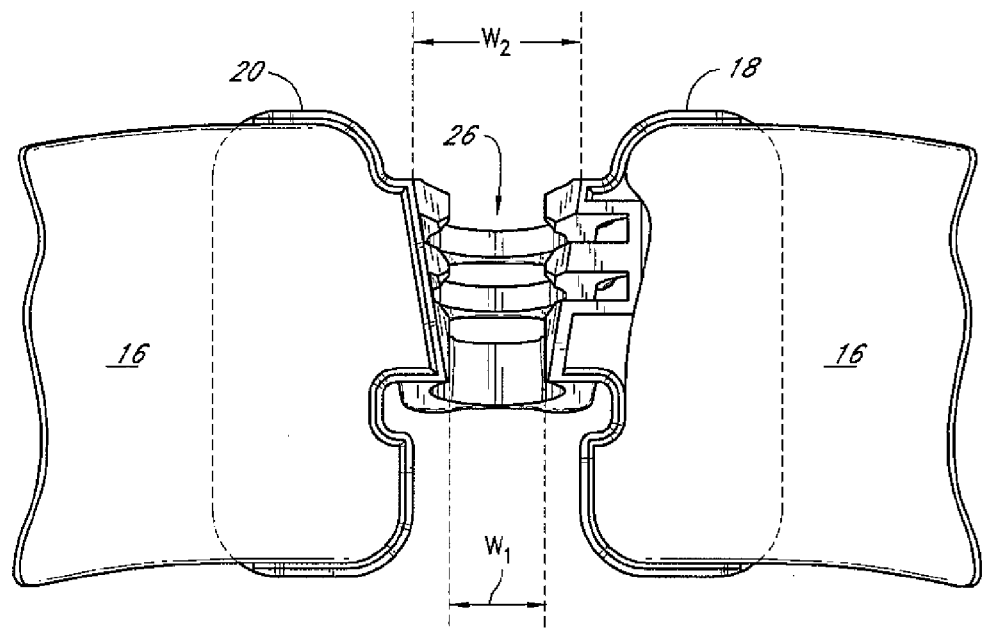
FIG. 6 is a bottom plan view of the retainer and portions of the securement members from FIG. 2 and illustrates that the distance between the side mounting wings varies in the region of the retainer.

As shown most clearly in FIGS. 3 and 6, the lower side of the retainer 14 includes an access or lower opening 26. In some forms, the lower opening 26 has generally tapering sides along the longitudinal axis to match generally the shape of the medical article. In other forms, the lower opening 26 has generally parallel sides while the channel 24 is tapered to match generally the shape of the medical article. The lower opening 26 may include contouring (e.g., chamfers) along its periphery in order to guide the medical article into the central channel 24 when inserting the medical article into the retainer 14.

Referring now to FIG. 5, the retainer 14 further comprises at least one retention surface 28 disposed on a lower side of the inverted channel 24. The retention surface 28 holds at least a portion of the retained medical article within the channel 24. This support can be provided by, for example, an adhesive, a region of the inverted channel which provides a degree of snap-fit with the retained medical article, two or more regions of the inverted channel which provide a degree of snap-fit with the retained medical article, or a combination of the adhesive and a region of snap-fit. The adhesive can be located on one or more surfaces of the retainer 14 that contact the medical article. For example, the adhesive could be located on the surface of the inverted channel or on an abutment.

As shown most clearly in FIG. 5, one form of the retainer 14 includes multiple pairs of retention surfaces 28. The corresponding retention surfaces of each pair lie on opposite sides of the access opening 26 from each other. In this form, the retention surface 28 is a portion of the surface that defines the central channel 24 and is located on the lower side of the central channel 24. One retention surface 28 is located to one side of the central axis; the other retention surface 28 is a portion of the surface that defines the central channel 24 and is located on the lower side of the central channel 24. Another retention surface 28 is further located to the side of the central axis that is opposite to the aforementioned retention surface 28, to form a pair of retention surfaces 28. Once the medical article is placed in the central channel 24, each opposing pair of retention surfaces 28 holds a portion of the retained section of the article within the channel 24. While multiple retention surfaces are illustrated in FIG. 5, retention surface 28 can be employed in variations of the illustrated retainer 14 and still support the medical article within the channel 24, as may be appreciated.

Pressure can be provided by the retention surfaces 28 which hold the medical article within the retainer 14. The retention surfaces 28 provide a degree of snap fit between the retainer 14 and the medical article. The degree of snap-fit can be increased by extending the overall surface of the central channel 24 through an arc of greater than 180°. As shown most clearly in FIG. 3, in one form, the arc extends for more than 180° in order to more firmly support the retained portion of the medical article. As shown, the walls of the central channel 24 extend through an arc of approximately 270°. The length of such an arc provides a snap-fit securement between the central channel 24 on the body member 22 and the secured portion of the medical article. In this way, the medical article can be placed in position prior to attaching the securement system 10 to the patient without concern that the medical article will shift while the healthcare provider is attaching the system 10 to the patient. Additionally, the releasable engagement provided by snap-fit connection also permits the retained portion of the medical article to be readily released from retainer 14.

Figure 7:
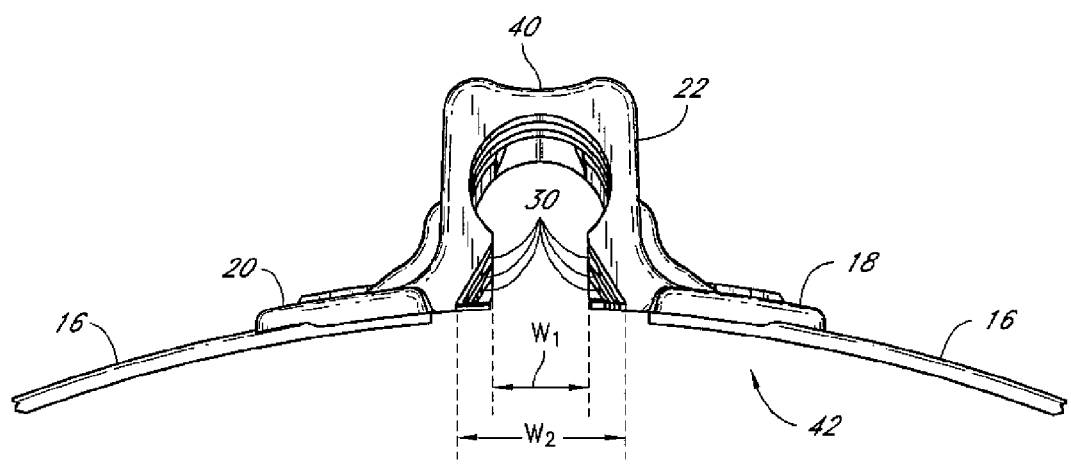
FIG. 7 is a rear side view of the retainer and portions of the securement members from FIG. 2.

Referring now to FIGS. 5 and 7, chamfered surfaces 30 are formed on the underside of the retainer body 22 along one of the lower edges of the access opening 26. A second set of chamfered surfaces 30 are formed on the underside of the retainer body 22 along the other lower edge of the access opening 26. The portions of the retainer body 22 between these chamfered surfaces 30 and the retention surfaces 28 form hips 32. In other words, the hips 32 are the portion of the body 22 that is defined by a lower side of the central channel 24 (either the retention surfaces 28 on one side of the central axis or the retention surfaces 28 on the other side of the central axis), the chamfered surfaces 30, and the sides of the narrow lower opening 26. In one form, the chamfered surfaces 30 on one side of the central axis are oblique to the chamfered surfaces 30 on the other side of the central axis and help guide the medical article into the lower opening 26 and the central channel 24.

The retainer 14 can include a generally rigid structure (at least in comparison to foam or tape) and is principally defined by the body member 22 and the mounting wings 18 and 20. The body member 22, however, may be somewhat flexible in nature, due both in part to its structure and to the material used to form the body member 22. Suitably rigid but flexible materials include, for example, but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials can be utilized.

The body member 22 and the mounting wings 18 and 20 are integrally formed to comprise a unitary retainer 14. This can be accomplished in any of a variety of ways well known to those skilled in the art. For instance, the entire retainer can be injection molded in order to reduce fabrication costs. The illustrated retainer 14 may be formed by injection molding using polyethylene or a polypropylene material. The retainer 14, however, can comprise a non-unitary body member 22 and mounting wings 18 and 20. In this manner, the body member 22 and one or both of the mounting wings 18 and/or 20 is formed separately and then coupled together. Additionally, the body member 22 and mounting wings 18 and 20 can have other forms and can have other orientations relative to one another. The body member 22 also can be clear or transparent to facilitate alignment of the retainer 14 with the catheter hub or other medical article during installation.

Each mounting wing 18 and 20 may include a glue dam around a portion of its periphery on its underside. The glue dam restricts adhesive flow beyond an inner edge of the respective mounting wing when an adhesive is employed to affix the securement member 16 thereto. The outer edge of each mounting wing 18 and 20 does not include the glue dam to allow any excess glue or adhesive to seep out from under the mounting wing during the manufacturing process in the lateral direction away from the retainer 14.

In the illustrated embodiment, the body member 22 of the retainer 14 is attached to an upper surface 34 of each securement strap 16 via the mounting wings 18 and 20, as is shown in FIG. 1. The body member 22 is desirably secured to the upper surface 34 of each securement strap 16 by a solvent bond adhesive, such as cyanoacrylate or other bonding material. One such adhesive is available commercially as Part No. 4693 from the Minnesota Mining and Manufacturing Company of Minneapolis, Minn.

When each securement strap 16 is secured to the patient, the medical article is inhibited from moving substantially in either the lateral or transverse directions relative to the patient. Longitudinal movement of the medical article is inhibited by engagement between at least one abutment surface on the retainer 14 and a contact surface or mating surface on the medical article. The abutment surface on the retainer 14 may extend generally normal to the axis of the central channel 24. The abutment surface can be located at or between the distal and proximal ends of the retainer 14. For example, the abutment surface can be either the proximal or distal ends of the retainer. Moreover, multiple abutment surfaces on the retainer 14 can be employed with each abutment surface being the same or a different type of abutment surface. Additionally, the abutment surface can be used to arrest movement in one longitudinal direction and the shape of the channel can be used to arrest movement in the opposite longitudinal direction. For example, at least a portion of the channel 24 can have a tapering inner surface and the retainer can include an abutment surface in the form of the proximal end of the retainer. The tapering shape and abutment surface cooperate to inhibit longitudinal motion in both longitudinal directions. In such an embodiment, the tapering surface contacts an outer tapering surface of the medical article to limit motion in one direction. Likewise, the proximal end of the retainer abuts with a radially extending member on the medical article to limit motion in the opposite direction.

The retainer 14 thus may include one or more abutment surfaces. In the illustrated embodiment, the retainer includes multiple abutment surfaces that are formed by one or more slots 36 in the body member 22. In the form of a slot 36, one abutment surface forms one side of the slot and another abutment surface forms the other side of the slot 36.

To arrest longitudinal motion in the illustrated embodiment, two contact surfaces in the form of a single radially extending member or tab 38 are employed on the medical article. The radially extending member 38 extends through the slot 36 in the retainer 14 to inhibit longitudinal motion of the medical article in both directions. The contact between the two abutment surfaces on the retainer 14 and their corresponding contact surfaces on the medical article arrests motion in the longitudinal direction. Further forms of the retainer 14 inhibit rotational movement of the installed medical article.

As shown in FIG. 2, the retainer 14 includes pairs of abutment surfaces with each pair forming one lateral slot 36 that are sized to receive a radially extending portion of the catheter 38 (e.g., a push tab that extends from a catheter hub). These slots 36 can extend circumferentially about at least a portion of the axis of the central channel 24. Each slot has a longitudinal length sufficient to accept the radially extending member of the retained medical article.

The radially extending portion of the medical article may be in the form of a push tab. An embodiment of a push tab is described with reference to FIG. 1. In particular, it can be desirable for the longitudinal length of each slot to be sufficient to receive the push tab 38 of the medical article; however, each slot 36 can be slightly larger than the thickness of the push tab 38 (as measured in the longitudinal direction) and a gap can exist between one or both sides of the push tab 38 and the corresponding abutment surfaces that define the slot 36 into which the push tab 38 has been inserted. In one form, at least two or three annular slots 36 are disposed within the retainer 14. The longitudinal length of each slot 36 may be about five thousandths of an inch (0.005 inch, 0.127 mm) larger than the radially extending member (e.g., the push tab 38). Such an arrangement can serve to minimize longitudinal movement of the retained portion (e.g., the tab 38 in FIG. 1) of the medical article. Accordingly, a small gap can exist between any abutment surface and a corresponding contact surface before the medical article is shifted relative to the retainer 14. Once shifted, however, further longitudinal movement is prevented by the interference between the contact surface and the abutment surface.

Those of skill in the art will recognize that each slot 36 need not have identical radial extent. The radial extent of each slot 36 need not be uniform about the axis of the central channel 24.

The inner edges of each slot 36 can be chamfered so as to ease the insertion of a radially extending member into any slot 36. By having the edges of each slot chamfered, it becomes possible to move a radially extending member 38 into a slot 36 even if the initial alignment between the center of the slot and the center of the radially extending member is not exact. The use of chamfered edges on the slots 36, as well as the presence of slots located at multiple longitudinal positions along the length of the central channel 24, allows for a medical article to be placed into the central channel of the retainer 14 with only coarse alignment with the axis of the central channel. The medical article generally moves into the nearest slot 36 as the medical article is pressed up into the retainer 14 from below (that is, as the retainer 14 is pressed over the retained portion of the medical article). The chamfered surfaces 30 adjacent to the mounting wings 18 and 20 help guide the medical article into the central channel 24. The alignment process is further facilitated when a portion of the retainer 14 is transparent.

As shown most clearly in FIGS. 3 and 7, an upper section of the retainer 140 further comprises a depression 40 which forms a finger pad that a healthcare provider can press down upon. The depression 40 encourages the finger to push down on the retainer 14 and discourages the healthcare provided from gripping the retainer 14 on its sides during application. Such a side grip could squeeze or constrict the retainer 14 and make it harder to slip the retainer 14 over the medical article. By pushing down on the retainer 14, this constrictive effect is avoided.

As illustrated in FIGS. 3 and 7, a base surface 42 of the retainer 14 can have a concave curved shape when viewed from the front and rear sides. The degree of curvature can be varied depending on the expected location of usage or application of the securement system 10. It will be appreciated that many common sites for insertion of medical lines which require securement will be located on anatomical regions exhibiting convex curvature, such as a dorsal side of a hand, a arm, a leg, a contact surface, etc. By providing a concave bottom profile to the retainer 14, the retainer will rock less once placed upon the patient via gel pads 12.

FIG. 4 is a side view of retainer 14. As illustrated in FIG. 4, an axis 44 of the central channel 24 lies at an angle with respect to the base surfaces 42 of the retainer 14. The desired angle between the medical article and the patient is created by angling the axis 44 of the central channel 24. This angle is selected in order to align the axis 44 of the channel 24 of the retainer 14 with the desired incident angle with which the medical article is to contact the skin of the patient. A variety of different angles can be used, ranging from 0° to 45° or from 5° to 25°. For instance, for the securement of intravenous catheters, it is desirable for the angle of incidence of the catheter to the skin of the patient to be between about 70 to about 15°. For the securement of arterial catheters, it is desirable for the angle of incident of the catheter to the skin of the patient to be about 12.5°. By angling the axis 44 of the channel 24 at the desired angle, which will depend upon the particular securement application (e.g., securing an arterial catheter, an intravenous catheter, etc.), the proper angle of incidence for a catheter can be maintained.

As illustrated in FIG. 2, the retainer 14 further comprises ribs 46. The ribs 46 project away from the outside surface of the channel 24. Such ribs 46 may be formed by extending portions of the slots 36 of the retainer 14 away from the channel 24. The ribs 46 provide additional surfaces for the healthcare provider to grip the retainer 14.

As shown most clearly in FIGS. 2 and 4 through 5, located adjacent to the slots 36 are upper sections 48. The thickness of the upper sections 48 in the longitudinal direction can vary in order to maintain a generally constant spring force along the entire length of the retainer 14. In this way, the same amount of force is required to spread the walls of the retainer 14 apart even though in the illustrated embodiment the back end of the retainer 14 spreads more to receive the larger diameter section of a tapered catheter hub. As illustrated in the cross-section view of FIG. 5, the longitudinal and transverse lengths of the upper sections 48 vary between one or more of the upper sections.

Although certain features of the retainer 14 can be specifically configured for use with a catheter hub, it will be understood by those of skill in the art that such a retainer 14 can be used with other adaptors or medical lines as well. Furthermore, the retainers described herein can be modified to more effectively cooperate with various types of connector fittings and adaptors.

As shown in FIGS. 2 through 7, each slot 36 is substantially annular in form. However, as illustrated in FIG. 2, a stop member or wall 50 may extend into the path of the one or more slots 36 at a circumferential location about the axis of the central channel 24. As shown in FIG. 2 wall 50 is located on the mounting wing 18 side of the retainer 14. Wall 50 limits the rotation of the radially extending member and medical article when the medical article is installed in the retainer 14. Thus, one or more slots 36 extend circumferentially about the axis of the central channel 24 for less than 360 degrees.

The wall 50 can be located at other locations around the circumference of the central channel 24. For example, the wall 50 could extend in a lateral direction away from the mounting wing 20 and into one or more slots 36. In forms of the retainer 14 where the wall 50 extends into less than all of the slots 36, the healthcare provider can select whether to restrict the rotation of the medical article. For example, the healthcare provider can restrict the rotation of the medical article by inserting a radially extending member of the medical article into a slot 36 that includes the wall 50. Alternatively, the healthcare provider can install the radially extending member into a slot 36 that does not include the wall 50 to allow unbridled rotation of the medical article. Moreover, more than one wall 50 can be located around the circumference of the one or more slots 36 to further limit the rotation of the medical article. In still further variations of the retainer, the retainer can omit the wall(s) 50.

Each slot 50 may have a lateral width sufficient to receive the radially extending member of the medical article. In this way, the retainer 14 is designed to grip non-winged catheters regardless of the position of the radially extending member. For example, as shown, a catheter hub can be installed into the retainer 14 regardless of rotation of the catheter hub about its axis except when the catheter hub is rotated such that the radially extending member coincides with the wall 50. The slot 36 can initially receive the radially extending member whether the radially extending member is pointing away from the patient, toward the patient, to either side, or generally at any other angle about the axis of the catheter hub. However, when the radially extending member is pointing directly to the left side and the catheter hub enters the opening 26, the radially extending member contacts the wall 50. As the catheter hub is further installed into the retainer 14, the catheter hub is forced to rotate such that the radially extending member is pointing downward. When the radially extending member is pointing downward, the radially extending member will follow the catheter hub into the retainer 14 as the catheter hub is inserted through the opening 26. Once the catheter hub has rotated and is subsequently fully installed in the retainer 14, the wall 50 will not allow the catheter hub and radially extending member to rotate completely about the axis of the central channel 24. For example, as the catheter adapter is rotated, the radially extending member of the catheter hub slides within the slot 36. However, at some point during the rotation of the catheter hub, the radially extending member contacts the wall 50

In the embodiment illustrated in FIGS. 2 through 7, the wall 50 limits the rotation of the radially extending member when the push tap is sufficiently rotated in either direction towards the mounting wing 18 side of the retainer 14. In this way, the wall 50 prohibits the catheter hub from 360-degree rotation while the catheter hub is installed in the retainer 14.

When the radially extending member points downward (e.g., toward the patient) and generally normal to the bottom surfaces of the retainer 14, the radially extending member extends through the lower opening 26. The hips 32 in the lower opening 26 are spaced sufficiently close to capture the radially extending member in this position and thereby inhibit longitudinal movement of the catheter hub.

FIG. 6 is a bottom plan view of the retainer 14 and illustrates that the distance between the side mounting wings 18 and 20 varies in the region of the retainer 14. Width W1 is measured between the side mounting wings 18 and 20 in a lateral direction as shown. Width W2 is measured between the side mounting wings 18 and 20 in a lateral direction as shown. FIG. 7 is a rear side view of the retainer 14 and further illustrates the widths W1 and W2 from FIG. 6. The side mounting wings 18 and 20 are designed so that width W1 is less than the width W2. Width W1 is selected to deter backward insertion of the medical article into the retainer 14. For example, the width W1 could be selected to be smaller than a spin nut or the connector end of the catheter hub. With W1 less than W2, the potential for the medical article being incorrectly inserted into the retainer 14 is reduced.

Medical Articles

An exemplary medical article for use with the embodiment of the securement device described above will now be described with reference to FIG. 1. The medical article can be a single medical article or a combination of one or more medical articles. Such medical articles can be or include, for example, but without limitation, connector fittings, catheters, catheter hubs, catheter adaptors, fluid supply lines, or other similar articles. FIG. 1 shows in a perspective view a catheter hub 52 and a connector fitting 54 with a spin nut 56. The connector fitting 54 may be disposed upon the end of a medical line 58 which can be connected to a drip bag, blood monitor, or other fluid related medical apparatus. While the retainer 14 is configured to receive a portion of the catheter hub 52, the retainer can be configured for use with the connector fitting 54, as will be described.

The connector fitting 54 comprises an elongated body 60 which is attached to the end of the medical line 58. The connector fitting 54 also comprises a portion that is tapered along at least part of its longitudinal length so as to allow the end of this region to fit within the tapered conical portion of an catheter hub 52. A tapered portion (not shown) of the connector fitting 54 also may include a centrally disposed lumen that communicates with the lumen of the medical line.

As indicated, FIG. 1 shows connector fitting 54 with the spin nut 56 secured in the proximal position and secured to the catheter hub 52. When the connector fitting 54 is inserted into the catheter hub 52, the lumen of the connector fitting is disposed in fluid communication with the lumen of the catheter hub 52. This provides fluid communication between the medical line 58 and the patient.

As shown, the connector fitting 52 has at least two contact surfaces in the form of one radially extending element 62 disposed upon an end of the elongated body 56 of the connector fitting 54 opposite the tapered end (not shown). It may be useful for the radially extending element 62 to extend completely around the circumference of the connector fitting 54. Additional contact surfaces in the form of a second radially extending element 64 can also be disposed upon the elongated body 56, as can additional radial elements (not shown). Those of skill in the art will recognize that the radially extending element or elements 62 need not have any particular shape or longitudinal thickness. Additionally, the radially extending elements need not have the same shape. For instance, the first radially extending element 62 can have the hexagonal shape illustrated and the second radially extending element 64 can have a circular shape.

A spin nut 56 is disposed upon the connector fitting 54 around the elongated body 320 of the fitting. The spin nut 56 is substantially cylindrical in form and is able to move upon the connector fitting 54. The spin nut 56 is capable of both rotational motion around the axis of the connector fitting and axial motion in both the proximal and distal directions along the length of the elongated body of the fitting 54. The spin nut 56 also includes internal screw threads.

Still referring to FIG. 1, a catheter hub 52 includes a body that, as shown, is configured as a catheter hub and has a generally conical shape and tapers from a large radius to a smaller radius along its length. The catheter hub 52 comprises two contact surfaces that together form a radially extending member. The radially extending member can be, for example, a lateral tab 38 which is disposed at a position along the length of the body of the hub 52. The tab 38 can be gripped by the healthcare provider from the upper side of the retainer 14 in order to immobilize the catheter hub 52 when unscrewing the spin nut 56 or otherwise disengaging the connector fitting 54 from the catheter hub 52.

The catheter hub 52 also can include an external screw thread on the outside of the conical body near the end with the larger radius. The screw thread can be used in association with the spin nut 56 of the connector fitting 54 in order to securely interconnect the connector fitting 54 and the catheter hub 52.

The at least one retention surface 28 supports the medical article so that the medical article is elevated in the retainer 14 such that the retained portion of the medical article (e.g., the retained portion of the catheter hub) may be raised above gel pad 12. Thus, the retainer 14 lifts and holds the retained portion of the catheter hub 52.

As may be appreciated, wall 50, described above, prohibits 360-degree rotational movement of the catheter hub 52 when the catheter hub 52 is installed in the retainer 14. When the catheter hub 52 is fully installed in the retainer 14, the push tab 38 extends in a direction away from the central axis 44 of the catheter hub 52 and into the slot 36.

A benefit of limiting the rotation of the catheter hub 52 when it is installed in the retainer 14 can be understood with reference to FIG. 1. In FIG. 1, the connector fitting 54 comprises an elongated body 60 which is attached to the end of a medical line 58. The other end of the elongated body 60 connects to the catheter hub 60. The push tab 38 is disposed at a position along the length of the body of the hub 52. A spin nut 56 is disposed around the elongated body 60 of the fitting 54. Internal screw leads within the spin nut 56 engage with an external screw thread on the catheter hub 52 in order to securely interconnect the connector fitting and the catheter hub 52.

With reference to FIGS. 2 through 7, since the push tab 38 will contact the wall 50 of the retainer 14 when the spin nut 56 is rotated less than 360 degrees, once the push tab 38 contacts the wall 50, the healthcare provider can connect or disconnect the elongated body 60 from the catheter hub 52 without having to also grip the tab 38. Once the healthcare provider rotates the fitting 54 in either direction so that the tab 38 contacts the wall 50, the catheter hub 52 is effectively immobilized in that direction such that further rotation of the catheter hub 52 in that direction is prohibited. Once immobilized, the healthcare provider can unscrew the spin nut 56 or otherwise disengage the connector fitting 54 from the catheter hub 52 with a single hand. While the use of two hands may be fine in certain circumstances when operating the spin nut 56, the retainer 14 allows the healthcare provider to use a single hand.

Similarly, when connecting or re-connecting the elongated body 60 to the catheter hub 52, the healthcare provider can initially rotate the push tab 38, via the spin nut 56, until the push tab 38 contacts the wall 50. Once the push tab 38 contacts the wall 50, the catheter hub 52 is immobilized which can enhance further connecting of the elongated body 60 to the catheter hub 52. In this way, the healthcare provider can continue to turn the spin nut 56 until the spin nut 56 is fully engaged with the catheter hub 52 without having to grip the push tab 38 or catheter hub 52.

The retainer 14 can be used with both luer slip and luer lock connector fittings, as those skilled in the art will plainly recognize. The retainer 14 is designed such that even with the push tab 38 positioned in the forward most slot 38, the retainer 14 can fit in the space defined between the push tab 38 and the spin nut 56 with the spin nut 56 fully engaged. The retainer 14 can be further sized to closely fit within this space to provide redundancy in arresting longitudinal movement of the catheter hub 52 relative to the retainer 14. Such slots 36 can also be disposed to extend longitudinally to accommodate radially extending members of greater longitudinal length, such as the splines of a Kipp-style connector.

Operation

An exemplary process for coupling a medical article with securement system 10 device described above will now be described with reference to FIGS. 1 through 9.

One method of using the securement system 10 will be described in the context of starting an intravenous line. However, the aspects and features of the operational method and the use of the present securement system 10 are not limited to this particular application.

A healthcare provider begins the procedure by inserting an IV catheter into patient's vein in a known manner and then attaching an intravenous line to the IV catheter though the luer connection. In particular, the healthcare provider inserts the tapered or luer end of the connector fitting 54 into the catheter hub 52 and then turns the spin nut 56 to thread the spin nut 56 over a thread flange disposed at the distal end of the catheter hub 52. This action draws together the two medical article components and releasably interlocks them. The immediate connection of the IV line to the catheter inhibits a back flow of blood through the catheter. The healthcare provider now secures the IV catheter in place on the patient using the securement system 10. In some variations of this method, however, the securement system 10 can be first be attached to one or both of the medical article (as well as the possibly to the patient) before the healthcare provider makes the connection between the two medical articles.

In order to illustrate more clearly the interaction between the retainer 14, the catheter hub 52, the gel pad 12 and the securement straps 16 of securement system 10, reference is made to FIG. 1 wherein an exploded perspective view of the securement system 10 is illustrated.

In use, the healthcare provider can secure a medical line 58 and the medical articles to a patient using the above-described securement system 10 or a modification thereof. The healthcare provider aligns the central channel 24 of the retainer 14 over the catheter hub 52.

As shown in FIG. 1, connector fitting 54 is secured to the catheter hub 52 with the catheter hub 52 inserted into the retainer 14. The lower opening 26 in the retainer 14 is pressed over the catheter hub 52 whereby the catheter hub fitting slides into the central channel 24 of the body member 22. Depending on the diameter of the catheter hub 52, the retention surfaces 28 can provide a snap-fit connection between the hub 52 and the body member 22. The contact surfaces of the catheter hub 52 may form one or more radially extending members 38 (e.g., one or more push tabs or annular collars), as shown. The radially extending member(s) 38 fits into one (or more) of the lateral slots 36 in the retainer 14. As can be seen, the tab 38 of the catheter hub 52 lies within one of the slots 36 of the retainer 14. In addition, the body of the catheter hub 52 generally lies within the central channel 24 of the retainer 14. When guided through the lower opening 26 by the healthcare provider, the body of the catheter hub 52 will lie within the central channel 24 of the retainer 14. The abutment surfaces of the slot 36 will inhibit longitudinal migration of the catheter hub 52 through the central channel 24 of the retainer 14.

In addition, if used with a connector fitting 54 in which a portion of the connector fitting, such as the spin nut 56, has a greater radial size than the size of the central channel 24 of the retainer 14, the spin nut 56 can act as a contact surface and will inhibit axial motion in one direction through the central channel 24 of the retainer 14 as well. Using the size of the spin nut 56 or other element having greater radial size than the size of the channel is not required for effective operation of the systems described herein; however, such a technique may be an effective form of securement or redundant securement in some applications.

The combination of the channel shape 24 (both the truncated circular shape and the tapering width), the top of the retainer 14, and the interengagement between the slot(s) 36 and the radially extending member(s) 38 on the catheter hub 52 arrest movement of the retained section of the medical line in three dimension: longitudinally, laterally and transversely. Further, the wall 50 prohibits the catheter hub 52 from 360-degree rotation while the catheter hub 52 is installed in the retainer 14. The rotational stop provided by the wall 50 allows the healthcare provider to attach and detach the spin nut 56 (and thus the connector fitting 54) to and front the catheter hub 52 without having the remove the catheter hub 52 from the retainer 14. This feature is optional and the wall 50 can be omitted from the securement system 10.

Once the catheter hub 52 or other medical article enters the lower opening 26 of the retainer 14, the high coefficient of friction, tacky gel pad 12, described above, is preferably positioned at the desired location upon the patient (e.g., on the patient's skin). The retainer 14 and medical article assembly is then placed upon the gel pad 12. In some embodiments, the gel pad 12 is first placed on the retainer 14 and the medical article assembly is then positioned at the desired location upon the patient. The gel pad 12 may be positioned on the retainer 14 either before or after the medical article has entered the lower opening 26 of the retainer 14.

The gel pad 12 may comprise first and second portions. The first portion may be configured to be placed on a patient. The first portion may comprise an adhesive surface. The second portion may be configured to connect to retainer 14. The first and/or second portions may comprise surfaces, such as an adhesive surface. The gel pad 12 may have at least two opposite sides (e.g., a top and bottom side). In some instances, the first portion comprises a surface on a first side (e.g., a bottom side) and the second portion comprises a surface on a second side (e.g., a top side), the first side being opposite to said second side. In some instances, the gel pad 12 comprises at least one border clearly differentiating the two sides, while in other instances, it does not.

A gel pad 12 may comprise a middle section formed of a material different from that of the first and/or second portions. For example, the first and second portions may comprise an adhesive material, while a middle section between the two portions does not comprise an adhesive material.

In some embodiments, the securement straps 16 are wrapped about the patient to secure the securement system 10 thereto. While a pair of securement straps 16 are shown affixed to the mounting wings 18 and 20 of retainer 14, it is also contemplated that a single strap 16 may be employed, the single strap 16 placed over the top of body 22 of retainer 14 and then wrapped about the gel pad 12 and patient and then securing the securement system 10 through the use of Velcro® or adhesive or the like. The securement strap 16 may comprise a band.

In other embodiments, the securement straps 16 are not included as part of the securement system 10. For example, the gel pad 12 may be configured to fix, restrain and/or stabilize the retainer on a patient.

As may be appreciated, the central channel 24 of the retainer 14 surrounds an arc length of more than 180 degrees of the medical article. This inhibits any transverse or lateral motion of the medical article relative to the retainer 14. The catheter hub 52 can be inserted into the retainer 14 either before or after the fitting connector is attached to the hub 52.

When securement system 10 is provided with a kit to form a gel pad 12 prior to use, one or more molds will be provided to enable the healthcare provider to form a gel pad 12 most effective for the intended patient use. At least two gel components, one comprising a catalyst, will be mixed and poured into the mold and cured. Once cured, the gel pad is ready for use.

As may be appreciated y those skilled in the art, other retainer designs may be employed and benefit from the systems and methods disclosed herein. For example the retainers taught in U.S. Pat. Nos. 5,693,032; 5,578,013; and 7,014,627; the contents of which are hereby incorporated by reference for all that they disclose, would be expected to benefit from the systems and methods disclosed herein.

All patents, test procedures, and other documents cited herein, including priority documents, are fully incorporated by reference to the extent such disclosure is not inconsistent with this invention and for all jurisdictions in which such incorporation is permitted.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure and the claims that follow.

What is claimed is:

1. A securement system for use with a medical article, comprising:
   a compressible gel pad for contacting the skin of a patient, said gel pad not forming an adhesive bond with the skin of the patient and comprising two legs extending from a central region disposed therebetween; and
   a retainer comprising a body member having a longitudinal length, a pair of mounting wings, and a longitudinal access opening disposed on an underside of the body member and extending the longitudinal length of the body member, the retainer being releasably secured in contact with the gel pad so as to be supported at least in part by the gel pad,
   wherein the body member includes a longitudinal channel formed through the body member and defining a central axis, and wherein at least a portion of the medical article is disposed between at least a portion of the retainer and the gel pad when the medical article is retained by the retainer, and wherein the gel pad is disposed so as to allow at least ingress into the channel through the longitudinal access opening when the gel pad is secured in contact with the retainer, the channel extending about the central axis for more than 180 degrees so as to receive the retained portion of the medical article.

2. The securement system of claim 1, wherein the body member is configured to retain at least a portion of the medical article so as to inhibit movement of the retained portion of the medical article relative to the retainer in at least one direction.

3. The securement system of claim 1, wherein said retained portion extends entirely through said channel, said longitudinal access opening being configured to allow at least ingress of at least said retained portion of said medical article into the channel.

4. The securement system of claim 1 further comprising at least one abutment extending generally normal to a central axis of said channel and configured to inhibit longitudinal movement of the medical article relative to the retainer.

5. The securement system of claim 1, wherein the gel pad comprises a soft, tacky elastomer.

6. The securement system of claim 1, wherein the gel pad is formed by curing an organopolysiloxane composition.

7. The securement system of claim 6, wherein the organopolysiloxane composition comprises:
- a vinyl-containing high viscosity organopolysiloxane or a blend of high viscosity vinyl-containing organopolysiloxanes;
- a low viscosity organopolysiloxane or a blend of low viscosity organopolysiloxanes;
- a reinforcing filler;
- a platinum catalyst; and
- a hydrogen containing polysiloxane copolymer.

8. The securement system of claim 7, wherein a molar ratio of hydrogen to vinyl radicals in the total composition is less than 1.2, such that after curing, the degree to which said tacky, reinforced polysiloxane elastomer is partially crosslinked is about 30 to about 90%.

9. The securement system of claim 6, wherein the organopolysiloxane composition has a hardness of about 5 to about 55 durometer units (Shore 00), a tackiness of about 0 to about 450 grams as determined by a POLYKEN probe tack tester or about 0 to about 7.6 cm (about 0 to about 3 inches) as determined by a rolling ball tack tester and a tensile strength of about 0.14 to about 5.52 mega Pascals (about 20 to about 800 pounds/square inch), a minimum elongation of about 250 to about 1100 percent and a tear strength of about 0.8 to about 35.2 kN/m (about 5 to about 200 pound/square inch).

10. The securement system of claim 6, wherein the organopolysiloxane composition comprises, based upon 100 parts total composition:
- 20 to 90 parts of a vinyl-containing high viscosity organopolysiloxane or a blend of high viscosity vinyl-containing organopolysiloxanes having no more than 25 mole percent of phenyl radicals and having a viscosity of 2,000 to 1,000,000 centipoise at 25° C. of the formula:

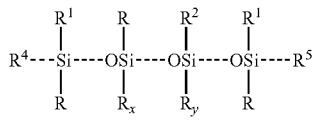

where $R^1$ is selected from the class consisting of alkenyl, alkyl and aryl radicals and R is a monovalent hydrocarbon radical, $R^2$ is selected from the class consisting of alkyl and aryl radicals, $R^4$ and $R^5$ are independently selected from the class consisting of alkyl and vinyl radicals; x varies from zero to 3000; and y varies from 0 to 300;
- from 5 to 40 parts of a polymer selected from the class consisting of a low viscosity organopolysiloxane and a blend of low viscosity organopolysiloxanes having viscosity that varies from 20 to 5,000 centipoise at 25° C. and having no more than 25 mole percent phenyl radicals of the formula

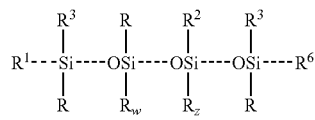

wherein $R^1$ and $R^6$ are independently selected from the class consisting of alkenyl, alkyl and aryl radicals, $R^2$ and R are as previously defined, $R^3$ is selected from the class consisting of alkyl, aryl and alkenyl radicals, w varies from 0 to 500, and z varies from 0 to 200;
- from 10 to 70 parts of a reinforcing filler;
- from 0.1 to 50 parts per million of platinum catalyst (as platinum metal) to the total composition; and
- from 0.1 to 50 parts of a hydrogen containing polysiloxane copolymer, wherein the molar ratio of hydrogen to alkenyl radicals in the total uncured composition is less than 1.2, such that after curing, the degree to which the soft, tacky, reinforced polysiloxane elastomer is partially crosslinked is about 30 to about 90%.

11. The securement system of claim 1 further comprising a securement member, the securement member being configured to secure the retainer relative to said patient.

12. The securement system of claim 11, wherein the securement member is releasably attachable to the patient.

13. The securement system of claim 11, wherein at least a portion of the securement member is attached to the retainer.

14. The securement system of claim 11, wherein the securement member wraps over at least a portion of the gel pad.

15. The securement system of claim 11, wherein at least a portion of the mounting wings is disposed between the body member and the gel pad at least when the retainer is secured to the patient.

16. The securement system of claim 15, wherein the securement member comprises a pair of straps, each strap being affixed to one of the pair of mounting wings.

17. The securement system of claim 16, wherein at least a portion of each strap is formed from a hook and loop type fastener.

18. The securement system of claim 1 further comprising a mounting surface, at least a portion of the mounting surface being covered with an adhesive.

19. The securement system of claim 18, wherein the mounting surface is disposed on the gel pad.

20. The securement system of claim 18, wherein the mounting surface is disposed on the retainer.

21. The securement system of claim 1, wherein the retainer extends in a direction away from the patient's body.

22. The securement system of claim 1, wherein the mounting wings are integral with the body member so as to form a unitary retainer.

23. The securement system of claim 1, wherein the mounting wings and the body member comprise separate structures coupled together.

24. The securement system of claim 1, wherein only the mounting wings contact the gel pad when the retainer is secured in contact with the gel pad, wherein the mounting wings compress at least a portion or each of the two legs of the gel pad.

25. The securement system of claim 24, wherein the medical article is disposed above the central region.

\* \* \* \* \*